US00PP37326P3

(12) United States Plant Patent
Baars

(10) Patent No.: US PP37,326 P3
(45) Date of Patent: Mar. 10, 2026

(54) OYSTER MUSHROOM VARIETY NAMED 'WUR SF3'

(50) Latin Name: *Pleurotus ostreatus*
Varietal Denomination: WUR SF3

(71) Applicant: Stichting Wageningen Research—Wageningen Plant Research, Wageningen (NL)

(72) Inventor: Johannes Jacobus Petrus Baars, Maasbree (NL)

(73) Assignee: Stichting Wageningen Research—Wageningen Plant Research, Wageningen (NL)

( * ) Notice: Subject to any disclaimer, the term of this patent is extended or adjusted under 35 U.S.C. 154(b) by 0 days.

(21) Appl. No.: 19/174,184

(22) Filed: Apr. 9, 2025

(65) Prior Publication Data

US 2025/0374841 P1 Dec. 4, 2025

(51) Int. Cl.
*A01H 15/00* (2006.01)

(52) U.S. Cl.
USPC ..... Plt./394
CPC ..... *A01H 15/00* (2013.01)

(58) Field of Classification Search
USPC ..... Plt./394
CPC ..... A01H 15/00; A01H 6/00; A01H 5/00
See application file for complete search history.

(56) References Cited

U.S. PATENT DOCUMENTS

PP18,037 P3 * 9/2007 Baars ..... A01H 15/00 Plt./394

* cited by examiner

*Primary Examiner* — June Hwu
(74) *Attorney, Agent, or Firm* — The Webb Law Firm

(57) ABSTRACT

'WUR SE3' is a new variety of oyster mushroom that produces no spores and has well-developed fleshy caps.

2 Drawing Sheets

Botanical classification: *Pleurotus ostreatus*.
Varietal denomination: 'WUR SF3'.

CROSS REFERENCE TO RELATED APPLICATION

The present application claims priority to European Community Plant Variety Rights Application No. 2024/1221, filed May 30, 2024, which is herein incorporated by reference.

BACKGROUND OF THE INVENTION

The present invention comprises a new and distinct cultivar of mushroom of the species *Pleurotus ostreatus* known by the varietal name 'WUR SF3'. The new variety was discovered in Wageningen, The Netherlands. The purpose of the breeding program was to develop a sporeless strain of oyster mushroom. The new variety has been trial and field tested and has been found to retain its distinctive characteristics and remain true to type through successive propagations.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
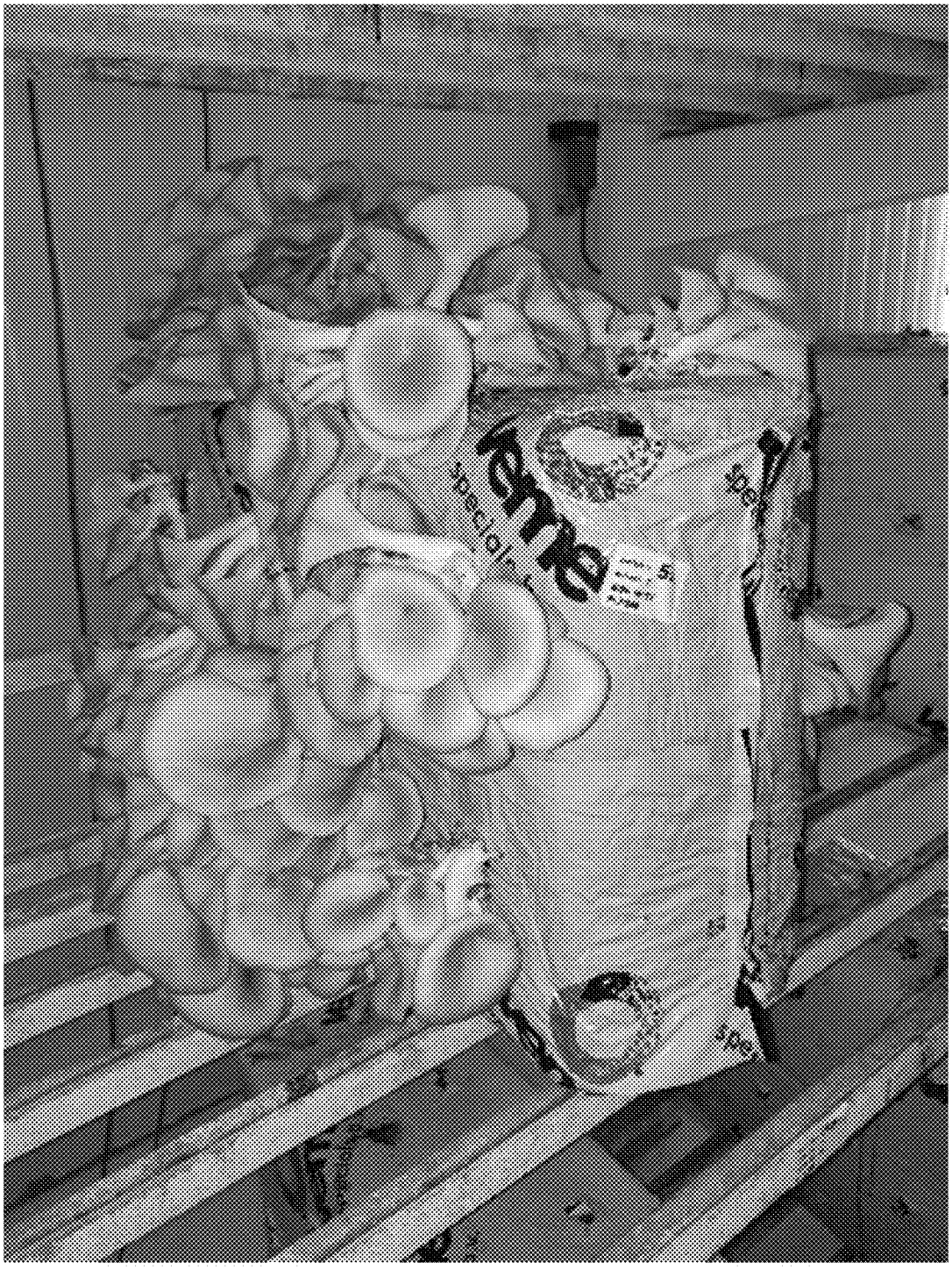
FIG. 1 shows a plurality of 'WUR SF3' mushrooms emerging from their growth medium.
Figure 2:
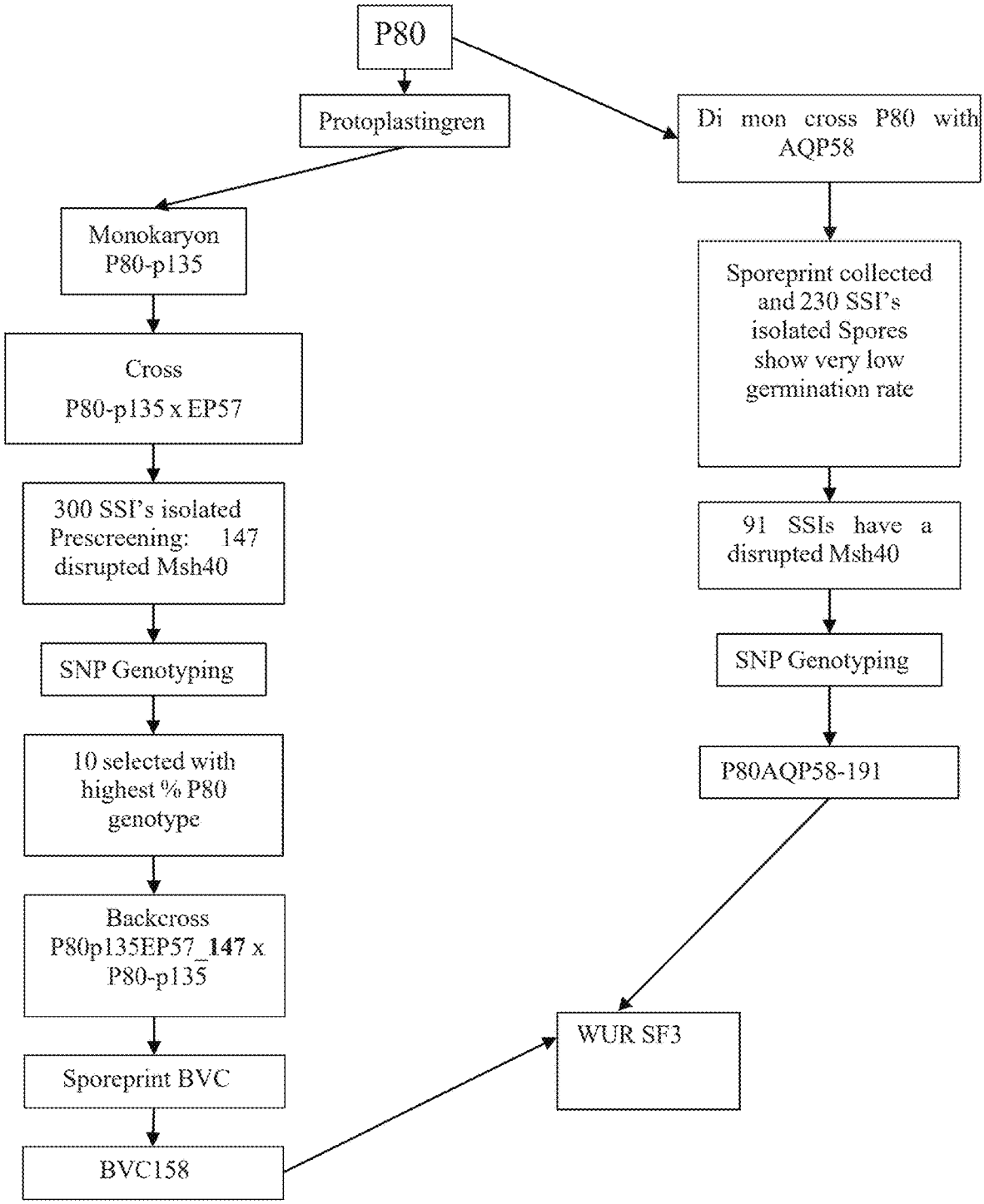
FIG. 2 shows a schematic of the breeding scheme of 'WUR SF3' mushrooms.

The following detailed description sets forth the breeding procedures and the characteristics of the new cultivar. As shown in Schematic 1, in breeding the new variety, parental lines were isolated from P80 (female parent; unpatented) and ATCC 58937 (male parent; unpatented). Both the male and female parent were protoplasted to obtain the constituent monokaryotic parental lines. In parallel breeding lines, the monokaryons of the male parent were used to introduce the sporeless trait into the parental monokaryons of the female parent. After this in both parallel breeding lines a backcross strategy was used to largely restore the genotype of both parental lines of the female parent, without losing the sporeless trait. The products (single spore isolates) of the parallel breeding lines were combined by mating to obtain the final product.

The new variety differs from the parents in that it does not produce basidiospores (unlike P80) and produces large and firm mushrooms (unlike ATCC 58937). The variety is similar to the female parent in that it produces large and firm sporulating mushrooms and is similar to the male parent in that it does not produce basidiospores. 'WUR SF3' slightly differs from another variety of sporeless Oyster mushroom, 'SPOPPO' (patented, U.S. Plant Pat. No. 18,037) in color of the mushroom cap. Next to this, required climate conditions to induce pinning differ, and the time needed between inoculation and production of the first flush is longer for the new variety. Characteristics that distinguish 'WUR SF3' from other varieties known to the breeder include:

Cap color

Time needed between inoculation of a pasteurized wheat straw-based substrate and production of the first flush Mushroom shape

Botanical Data Collection Conditions and Standards

The color standard used in the present application is the L*a*b* method (also designated as CIE.LAB or CIE-L*a*b*) defined by "Commission International de l'Eclaire" in 1976. The location where measurements were made was Wageningen, The Netherlands. Light conditions where measurements were made were by artificial light provided by a Minolta Chroma Meter type CR-200.

Growth Conditions

The variety was cultivated on a commercially available pasteurized wheat straw substrate. After pasteurization the substrate was inoculated with 30 liter of spawn per 1000 kg Fresh Weight substrate and pressed in 20 kg blocks wrapped in microperforated plastic foil. A total of 20 large perforations (1 cm diameter) were made per substrate block to provide room for the future development of primordia and subsequently, fruiting bodies. Spawn-run was performed at a substrate temperature aimed at 28° C. and relative humidity of 75%. When the substrate temperature exceeded 32° C., the air temperature in the growing room was lowered. After 18 days of spawn-run the growing room was vented in 2½ days to an air temperature of 14° C., a relative humidity of 93% and a $CO_2$ level of 850 ppm to induce primordia. At the appearance of primordia, the relative humidity was lowered to 90-92%. During maturation of the fruiting bodies, the relative humidity was lowered further to 88%. Mature mushrooms were harvested just before the rim of the mushroom starts to fold upwards. Immature mushrooms are usually not harvested commercially. Mushrooms of 2-3 cm cap diameter were used as representative for immature mushrooms.

Botanical Description

Age of described plant: Oyster mushrooms are generally produced within 5 weeks after inoculation of the straw substrate. The Oyster mushrooms are produced as a bundle of mushrooms varying in size. This limits the possibilities for a uniform description of the mushrooms. Here, photographs were taken just before harvest (harvested as commercial quality mushrooms).

Cap:

*Shape*.—Convex — strongly convex.

*Diameter*.—Range of 0.5-20 cm. Average of 7-8 cm (measured according to UPOV Test guideline 291/1, 2013 Mar. 20, mushroom size depends on cultivation format).

*Rim*.—The rim of the mushroom is folded downwards as long as the mushroom is still increasing in size. Mushrooms are normally harvested just before the rim of the mushroom starts to flip upwards. When fully matured, the rim is folded upwards completely. Lamellae of the mushroom run from the base of the stipe all the way up to the margin of the mushroom. The mushrooms tend to be a bit more darkly colored in the center of the mushroom (at the site of attachment of the stipe) and a bit more lightly colored at the rim. Color measurements are usually done on the rim at about 1-2 cm from the margin.

*Color*.—Immature: L=68-71, a=−1.9-1.2, b=15-17 (colors vary with temperature at which the mushroom is grown and with the light conditions. Values are given for artificial lighting in a growing room). Mature L=71-75, a=−1.3-1.9, b=11.3-15.4 (color varies with temperature at which the mushroom is grown and with the light conditions. Values given are for artificial lighting in a growing room).

*Flesh color*.—L=89-97.

*Flesh thickness*.—Immature: Flesh thickness with lamellae is 6-8 mm. Flesh thickness without lamellae is 5-6 mm. Flesh thickness with and without lamellae is measured perpendicular to the surface of the cap at the attachment of the stipe. Mature: Flesh thickness with lamellae is 12-14 mm. Flesh thickness without lamellae is 10-11 mm. Flesh thickness with and without lamellae is measured perpendicular to the surface of the cap at the attachment of the stipe.

*Texture*.—Firm.

*Height*.—Average range of 50 to 60 mm (height varies with diameter of the cap. Typically the bigger the diameter, the larger the height).

Lamellae:

*Characteristics*.—L=74-83, long-decurrent extending down on to the stipe, edge smooth, later somewhat undulating.

*Length*.—38-43 mm.

*Width*.—4-6 mm.

*Spacing*.—16-18 lamellae per cm (measured about halfway the length of the lamellae.

Stipe:

*Placement*.—Slightly excentric.

*Shape*.—Cylindric.

*Size*.—Length of 30-50 mm (measured according to UPOV Test Guideline 291). Stipe length is variable crop-to-crop and is influenced by the carbon dioxide levels in the air in the growing room. Diameter of 13-17 mm (measured according to UPOV Test Guideline 291).

*Texture*.—Fleshy, fibrous.

*Pubescence*.—None.

*Color*.—Immature: L=79-95. Mature: L=79-95.

Spores: None present.

Veil: No veil present.

General

Fruit body clusters: Present.

Disease resistance: Not determined.

Average harvest time: 28-32 days from spawning.

Odor: No strong odor. Very slightly anisum-like.

Shipping/storage quality: Mushrooms hold well in cold storage for 1-1.5 weeks.

Temperature tolerance: Between 0 and 35° C. when grown vegetatively.

I claim:

1. A new and distinct variety of mushroom named 'WUR SF3', substantially as described and illustrated herein.

* * * * *